US008651007B2

(12) United States Patent
Adams (10) Patent No.: US 8,651,007 B2
(45) Date of Patent: *Feb. 18, 2014

(54) BRANCHED STENT/GRAFT AND METHOD OF FABRICATION

(71) Applicant: AGA Medical Corporation, Plymouth, MN (US)

(72) Inventor: Daniel O. Adams, Long Lake, MN (US)

(73) Assignee: AGA Medical Corporation, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/835,534

(22) Filed: Mar. 15, 2013

(65) Prior Publication Data

US 2013/0204354 A1    Aug. 8, 2013

Related U.S. Application Data

(60) Continuation of application No. 13/197,526, filed on Aug. 3, 2011, now Pat. No. 8,434,393, which is a division of application No. 11/823,430, filed on Jun. 27, 2007, now Pat. No. 8,048,147.

(51) Int. Cl.
*D04C 1/06* (2006.01)

(52) U.S. Cl.
USPC ............................................................ 87/11

(58) Field of Classification Search
USPC ......... 87/5, 7, 8, 9, 11, 13, 34; 623/1.15, 1.16
See application file for complete search history.

(56) References Cited

U.S. PATENT DOCUMENTS

| 5,361,674 | A | 11/1994 | Akiyama et al. |
| 5,398,586 | A | 3/1995 | Akiyama et al. |
| 5,725,552 | A | 3/1998 | Kotula et al. |
| 6,409,750 | B1 | 6/2002 | Hyodoh et al. |
| 6,622,604 | B1 | 9/2003 | Chouinard et al. |
| 6,652,571 | B1 | 11/2003 | White et al. |
| 6,685,738 | B2 | 2/2004 | Chouinard et al. |
| 6,953,475 | B2 | 10/2005 | Shaolian et al. |
| 7,004,967 | B2 | 2/2006 | Chouinard et al. |
| 7,435,254 | B2 | 10/2008 | Chouinard et al. |
| 8,048,147 | B2 * | 11/2011 | Adams .................. 623/1.35 |
| 8,434,393 | B2 * | 5/2013 | Adams ....................... 87/11 |
| 2004/0138736 | A1 | 7/2004 | Obara |
| 2005/0033416 | A1 | 2/2005 | Seguin et al. |
| 2005/0234542 | A1 | 10/2005 | Melsheimer |
| 2006/0129222 | A1 | 6/2006 | Stinson |
| 2006/0161244 | A1 | 7/2006 | Seguin |
| 2007/0106375 | A1 | 5/2007 | Vonderwalde |
| 2007/0168019 | A1 | 7/2007 | Amplatz et al. |

(Continued)

OTHER PUBLICATIONS

Mexican Office Action for Application No. MX/a/2007/014643, dated Apr. 19, 2013.

*Primary Examiner* — Shaun R Hurley
(74) *Attorney, Agent, or Firm* — Armstrong Teasdale LLP (57) ABSTRACT

Branched braided stent or graft devices and processes for fabrication of the devices are disclosed in which a trunk portion and two hinge leg portions are fabricated in one piece braided from a single plurality of filaments, whereby the legs contain the full plurality of filaments and the trunk portion contains a subset of the same plurality of filaments. The fabrication process involves braiding the hinged legs on a mandrel while retaining loops of filament between the hinged leg portions for subsequent braiding of the trunk portion of the stent or graft.

20 Claims, 3 Drawing Sheets

(56) References Cited

U.S. PATENT DOCUMENTS

2009/0005847 A1\* 1/2009 Adams ........................ 623/1.2
2009/0188380 A1\* 7/2009 Dow et al. ...................... 87/11
2010/0063578 A1 3/2010 Ren et al.
2010/0137969 A1 6/2010 Rakos et al.
2011/0283871 A1\* 11/2011 Adams .............................. 87/9

\* cited by examiner

BRANCHED STENT/GRAFT AND METHOD OF FABRICATION

CROSS-REFERENCE TO RELATED APPLICATIONS

This application is a continuation of U.S. application Ser. No. 13/197,526 (now U.S. Pat. No. 8,434,393), filed Aug. 3, 2011, titled "Branched Stent/Graft and Method of Fabrication," which is a divisional of U.S. application Ser. No. 11/823,430 (now U.S. Pat. No. 8,048,147), filed Jun. 27, 2007, titled "Branched Stent/Graft and Method of Fabrication," each of which is hereby incorporated by reference herein in its entirety.

BACKGROUND OF THE INVENTION

1. Field of the Invention

The present development relates generally to stent or graft devices for implantation in an anatomical structure and, more particularly, to intravascular catheter deliverable branched stent or graft devices and methods of fabrication. Embodiments include unique branched stent or graft devices for the treatment of abdominal aortic aneurysms (AAA) involving the aorta-iliac bifurcation by reinforcing, excluding, bridging, or lining the diseased vessel, and to methods of fabrication of such as stent or graft devices involving a unique braiding technique using a single plurality of filaments to form two hinged legs and the common body or trunk portion of the device.

2. Description of the Related Art

An aortic aneurysm is a weak area in the wall of the aorta, the main blood vessel that carries blood from the heart to the rest of the body. The aorta extends upwards from the heart in the chest and then arches downwards, traveling through the chest (the thoracic aorta) and into the abdomen (the abdominal aorta). The normal diameter of the abdominal aorta is about one inch (2.5 cm).

Aortic aneurysms are frequently caused by the breakdown of the muscular layer and the elastic fibers within the wall of the aorta. The breakdown usually occurs over time, frequently in patients over 40 years of age, and can be caused by prolonged high blood pressure, effects from smoking or a genetic predisposition. As the vessel tissues deteriorate, the vessel wall strength decreases, and the high blood pressure causes the aortic wall to stretch beyond its normal size, forming an aneurysm. The weak aneurysm bulges like a balloon over time and can burst if the wall becomes too thin and weak to hold the blood pressure.

Most commonly, aortic aneurysms occur in the portion of the vessel below the renal artery origins. The aneurysm may extend into the aorta-iliac bifurcation and into the iliac arteries supplying the hips, pelvis and legs.

Once an aneurysm reaches 5 cm (about 2 in.) in diameter, it is usually considered necessary to treat to prevent rupture. Below 5 cm, the risk of the aneurysm rupturing is lower than the risk of conventional surgery in patients with normal surgical risks. The goal of therapy for aneurysms is to prevent them from rupturing. Once an AAA has ruptured, the chances of survival are low, with 80-90 percent of all ruptured aneurysms resulting in death. These deaths can be avoided if the aneurysm is detected and treated before it ruptures and ideally treated at an early stage (smaller aneurysm) with a lower risk procedure.

AAA can be diagnosed from their symptoms when they occur, but this is often too late. They are usually found on routine physical examination, through use of ultrasound, or by chest and abdominal X-rays. On examination, a doctor may feel a pulsating mass in the abdomen. If the doctor suspects an aneurysm, he/she will probably request that an ultrasound scan be carried out. Other scans, such as computerized tomography (CT) and magnetic resonance imaging (MRI) may also be performed. These scanning techniques are very useful for determining the exact position of the aneurysm.

The surgical procedure for treating AAA involves replacing the affected portion of the aorta with a synthetic graft, usually comprising a tube made out of an elastic material with properties very similar to that of a normal, healthy aorta. This major operation is usually quite successful with a mortality of between 2 and 5 percent. The risk of death from a ruptured AAA is about 50%, even during surgery.

More recently, instead of performing open surgery in undertaking aneurysm repair, vascular surgeons have installed an endovascular stent/graft delivered to the site of the aneurysm using elongated catheters that are threaded through the patient's blood vessels. Typically, the surgeon will make a small incision in the patient's groin area and then insert a delivery catheter containing a collapsed, self-expanding or balloon-expandable stent/graft to a location bridging the aneurysm, at which point the stent/graft is delivered out from the distal end of the delivery catheter and allowed or made to expand to approximately the normal diameter of the aorta at that location. The stent/graft, of course, is a tubular structure allowing blood flow through the lumen thereof and removing pressure from the aneurysm. Over time, the stent/graft becomes endothelialized and the space between the outer wall of the stent and the aneurysm ultimate fills with clotted blood. At this time, the aneurysm is no longer subjected to aortic pressures and thus will not continue to grow.

In treating AAAs that involve the aorta-iliac bifurcation, various stent or grafts designs have been placed to support, bridge or reline the vessels in the aneurysm segments. This has often involved multiple self expanding stents or stent grafts such as a large diameter stent or graft in the aortic segment and two smaller stents or grafts placed in each of the iliac arteries. In other designs the stent or graft has been designed to extend from the aortic segment into one branch of the iliac artery. In this case a hole is provided in the stent or graft to accommodate blood flow to the other iliac artery. A second stent or graft may be optionally placed into the other iliac artery and extending into the hole in the first stent or graft provided for iliac branch blood flow.

It has become apparent through use and clinical experience that the junctions of multiple stents or grafts presented placement problems of component alignment within the body. The stents or grafts being independent of each other caused components to rub against each other causing metal fatigue and flow discontinuities or thrombosis could occur where one component was not aligned with another and protruded into the blood flow. Use of multiple components also caused uneven vessel support such as where overlapping components may have an excess in vessel support as well as unsupported portions of the vessel where gaps occur between components. In the case of grafts, gaps between components cause leaks and may result in continued blood pressure exposure to the aneurysm.

As a result there remains a need for an alternative one piece stent or graft designs that covers the entire aneurysm segments including the main aortic segment as well as both iliac artery segments. It is also desirable that such a design be collapsible for percutaneous catheter delivery to the treatment site as well as self expandable when deployed from the delivery catheter.

U.S. Pat. No. 6,409,750 to Hyodoh et al. discloses woven bifurcated and trifurcated stents together with methods of fabrication. Those devices include a first plurality of wires defining a first leg having a first portion and a second plurality of wires defining a second leg having a second distal portion, and a common body having a distal end and a proximal portion, the common body being formed from at least the first and second plurality of wires, the proximal portion of the common body being adjacent to the distal portions of both legs, and both ends of at least one wire from both of the pluralities being located proximate the distal end of the common body. In this design the braided legs are connected only by the common body portion and gaps in metal coverage occur near the juncture of the legs.

U.S. Pat. No. 7,004,967 to Chouinard et al. describes a process for manufacturing a braided bifurcated stent. The process involves the use of two or more braiding machines in which a first discrete plurality of filaments are braided to form a first leg, and a second discrete plurality of filaments are braided to form a second leg. The process involves braiding the first plurality of filaments and the second plurality of filaments together to form the body using another braiding machine. That design results in metal coverage gaps occurring at the outside top portion of each leg and the process requires the use of multiple braiding machines. As with other concepts, the legs are not connected except to the common body portion. There are no common wires from one leg connecting to the other leg so a gap occurs between them.

There exists a need for a one piece branched stent or graft device that has improved metal coverage for uniform properties and a manufacturing process that is simple and produces a one piece design from a single discrete plurality of wires. There is a need for an improved bifurcated stent or graft that incorporates wires from one leg into the other leg creating a wire hinge and reinforcing the crotch area of the device. There is also a need for a device having the improved characteristics as above and which is also deliverable using a percutaneous intravascular catheter approach having a collapsed configuration for delivery through a catheter and a self expanding configuration when released from the catheter confines. The present development provides such a device.

SUMMARY OF THE INVENTION

The present concept includes embodiments of catheter-deliverable, endovascular, one piece, multi-region stent or graft devices. Embodiments include bifurcated stent or graft devices for treating abdominal aortic aneurysms involving the aorta-iliac bifurcation. An important aspect of the concept includes a braiding fabrication technique that enables a single bundle or a single plurality of filaments to be used to form a plurality of regions, such as distinct regions of a device including a first region, a second region and a third region.

One preferred embodiment, for example, includes three regions: the first region and second region form two hinged legs and a third region forms a common body or trunk portion of the device. The third region is braided from a subset of the same single plurality of filaments forming the two hinged legs. In this manner, the stent or graft structure includes a single plurality of resilient filaments that are braided to define a pair of hinged legs and a common body or trunk. The stent or graft has a filament hinge in the crotch area connecting the legs. The filaments are preferably a shape memory metal such as nitinol wire but may be or may include other metals that have an elastic heat settable shape. A polymer filament overlaying version can be used as part of a grafted device.

As used herein the terms "filament" and "wire" are used interchangeably to describe strands of any suitable type of material including metal and non-metal materials used in aspects of the devices. As used herein, the term "braiding" includes interweaving where appropriate. It will be appreciated the term includes any braid or weave which enables elongation of the device with corresponding reduction in diameter so that the device may be delivered by vascular catheter.

One preferred method of fabrication includes braiding a plurality of highly elastic filaments supplied from a plurality of braiding spools onto an assembled two-piece or two-part mandrel. The filaments are braided onto a first part of the mandrel to form a first leg. The braiding is stopped and the braid is secured around the mandrel at the first leg distal end (last braided portion) using tape or other clamping means.

Long loops are formed from each filament exiting the tape/clamp above the distal end of the leg except for filaments that are intended to be the crotch or hinge filaments or wires connecting the legs. The filament loops created are made long enough to later be braided into the common body portion or trunk of the stent or graft. Once the loops are formed, they are coiled or spooled and secured to be out of the way so as not to become entangled in continued braiding. The loop end is taped/clamped to the mandrel on top of the loop starting point. The braiding process is restarted and a second leg is braided over a second part of the mandrel using the same plurality of filaments that were used to braid the first leg.

Once the second leg has been braided to a desired length, the filaments are taped/clamped to the mandrel and cut from the braiding spools. The braid and mandrel are removed from the braiding machine. The two parts of the two-piece assembled mandrel are separated and the legs and first and second mandrel parts are manipulated in relation to each other to position the legs adjacent each other connected by the hinge filaments. Next, a common body portion or trunk mandrel is attached using leg extensions designed to be inserted into the top of each leg mandrel. The loops that were formed and coiled or spooled are then made available for braiding the common body portion or trunk of the stent/graft.

At this point, a plurality of trunk braiding options are available and a decision is now required to determine which variation of braiding the trunk is to be selected. One option or choice is to leave the spooled loops intact and braid both filaments of each loop along the same path. A second choice is to unwind the loops, sever the end of each loop and rewind the two filaments onto separate braiding spools. The two braided loop filaments can then be wound in opposite helical directions.

In either braiding choice the filaments are spooled and placed on the braiding machine spool carriers and the new mandrel assembly is installed in the braiding machine. The common body portion or trunk is then braided using a major portion of the same plurality of filaments used to braid the legs. The remaining portion of the plurality of filaments or those not used to braid the trunk, are the filaments selected to form the hinge connecting the legs. The braiding machine for braiding the trunk will require a different number of spool carriers as compared to the leg braiding. In the case of the loops being severed into two pieces, for example, the number of braiding machine spool carriers will be much higher in number than if the loops are left intact.

Aspects of the inventive concept encompass both the method of fabrication of the branched stent or graft device and also the medical device that results from use of the process.

DETAILED DESCRIPTION OF THE PREFERRED EMBODIMENTS

Embodiments will next be described with reference to the drawing figures. Such figures and the accompanying detailed description are meant to be illustrative rather than limiting and are included to facilitate the explanation of aspects of the inventive concepts, including devices and methods of fabrication of the devices.

Figure 6:
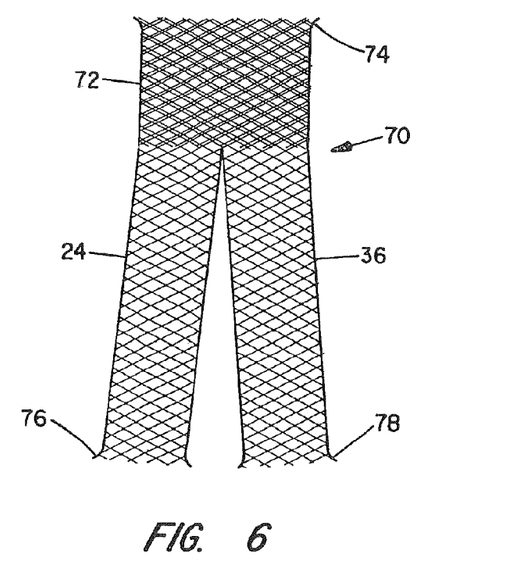
FIG. 6 is a side view of one embodiment of a final device.
Figure 7:
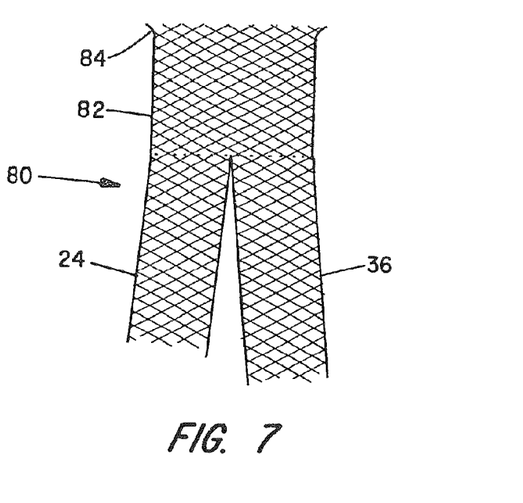
FIG. 7 is a side view of an alternative embodiment.

Two preferred final device configurations of a branched stent/graft are shown in FIGS. 6 & 7. These embodiments consist of two leg portions formed with a common body or trunk portion.

One aspect of the development involves the materials of construction of a device contemplated by the present invention. The device is fabricated from a single plurality of filaments which in the preferred embodiment should include a material which is both resilient and which can be heat treated to substantially set a desired shape. Materials found suitable for this purpose include a cobalt-based low thermal expansion alloy referred to in the field as Elgeloy, nickel-based high temperature high-strength "superalloys" commercially available from Haynes International under the trade name Hastelloy, nickel-based heat treatable alloys sold under the name Incoloy by International Nickel, and a number of different grades of stainless steel. The important factor in choosing a suitable material for the filaments or wires is that the filaments retain a suitable amount of the deformation induced by a molding surface when they are subjected to a predetermined heat treatment.

One class of materials which also meet these qualifications includes so-called shape memory alloys such as nitinol, an approximately stoichiometric alloy of nickel and titanium, which may also include minor amounts of other metals to achieve desired properties. Such alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration unless constrained from so doing.

Figure 8:
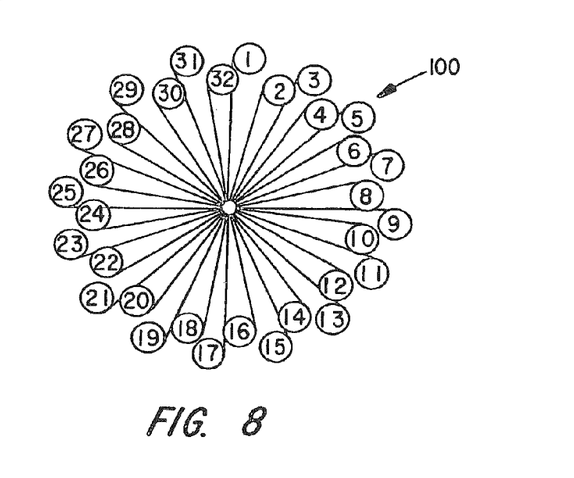
FIG. 8 is a schematic top view illustrating a 32 filament braider showing the spool carriers 1-32.

As an example, without limitation, the device can be illustrated being fabricated from 32 braided nitinol wires having a diameter ranging from 0.0015-0.008 inch (0.0381-0.203 mm), preferably 0.002-0.005 inch (0.051-0.127 mm). The number of wires to be braided may range from 4-200 or more, preferably from 8 to 144 and, more preferably, from 16-72 depending on the particular device characteristics desired. FIG. 8 shows a schematic top view illustrating 32 numbered spool carriers on a braiding machine 100. All the even numbered spool carriers travel in one direction (clockwise) and all the odd numbered spool carriers travel in the opposite direction (counter-clockwise). In addition, as the spool carriers travel in a circular direction, they also change radius of travel about the center of the braider passing inside of one spool carrier and outside of the next spool carrier, thereby forming wires wrapped about a center mandrel that are woven over and under each other in a braided configuration. As the spool carriers are moving, the mandrel is slowly moved in a vertical direction at a controlled speed relative to the braider speed to set the pitch of the braided wires. A typical pitch angle may range from 30-70 degrees from the longitudinal axis of the braided tube in the, as braided, relaxed tube prior to heat treatment. The pitch, pick count (number of wire crossovers per inch, or other lineal measure) and wire diameter, are all variables that can be altered to change the device characteristics as well as the heat set shape.

Figure 1:
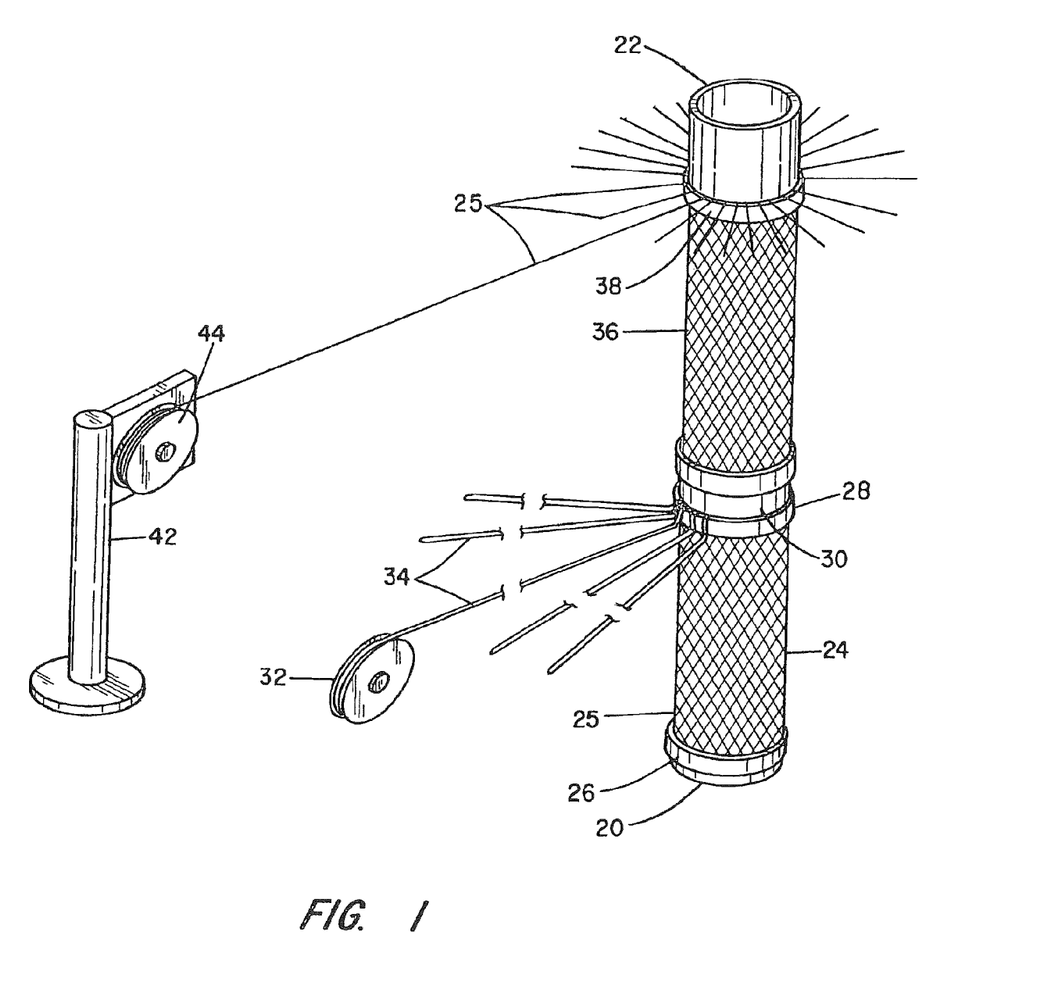
FIG. 1 is a schematic illustration of the braiding of both legs of a branched stent or graft device over an assembled two-part mandrel and showing the formation of loops between the leg segments.

Referring now to FIG. 1, there is shown a tubular mandrel consisting of two parts 20 and 22. The two-piece mandrel may be assembled together by sliding the two parts over a close fitting shaft and holding them in place with removable end caps (not shown) or by any number of other known suitable means. The braiding of a first region or leg 24 begins at the bottom of the mandrel as indicated in the illustration. The braid starts by attaching, as by taping or clamping, the thirty-two filaments or wires 25 to the mandrel as at 26. The braiding is begun at a controlled pitch until a desired sufficient length is generated for the first leg 24 near the center of the assembled mandrel. The braiding is stopped and the braided wires are next taped or clamped in place on the mandrel at location 28.

After the braiding of the first leg 24, a hinge zone 30 that represents the portion of the circumference of the first braided leg 24 to be connected directly to the second braided leg 36 is designated. In a preferred arrangement using the illustration of a thirty-two filament or wire braid, this will typically range between about 4 to 8 wires or from 4/32 to 8/32 (1/8 to 1/4 of the total) of the circumference of the legs based on the thirty-two filament braid. As an example, 4 wires may be designated as the hinge area 30. That leaves (32−4) or 28 remaining wires of the braid that will be configured differently.

Each of the remaining 28 wires leading from the spool carriers as at 32 will have a specific length of filament or wire drawn off the spool to form a loop as at 34 of wire, the loop beginning at the taped mandrel at 28 (end of leg one) and ending back at the same spot at the mandrel. The loop length is predetermined and is at least the length needed to braid the common body portion plus leader length for a braiding machine. The loops 34 are taped to the mandrel over the first tape at location 28 such that the wire leading back to the spool carrier as at 32 is at the same position as it was prior to the forming of the loop. After each loop 34 is secured, the loop material may be spooled or otherwise routed away from the braiding action to prevent the filament or wire from becoming entangled with the next braiding process.

It will be appreciated that all 32 wires are still oriented radially about the mandrel to begin braiding the second leg 36 from taped filaments as also shown in FIG. 1. The braiding is started at about mid point on the assembled mandrel and continues until the desired braided length for the second leg 36 has been completed. At this point, both ends of the leg 36 braid are secured to the mandrel by tape 38 and 40 (FIG. 2) or other clamping means. Next, the 32 wires from the spool carriers may be cut about 2 inches (5.1 cm) from the mandrel and the assembled mandrel and braided legs may be removed from the braiding machine along with the 28 loops of braid filament or wire. A typical filament feed spool is shown at 44 mounted on a spool carrier device 42 in a well known manner.

Figure 2:
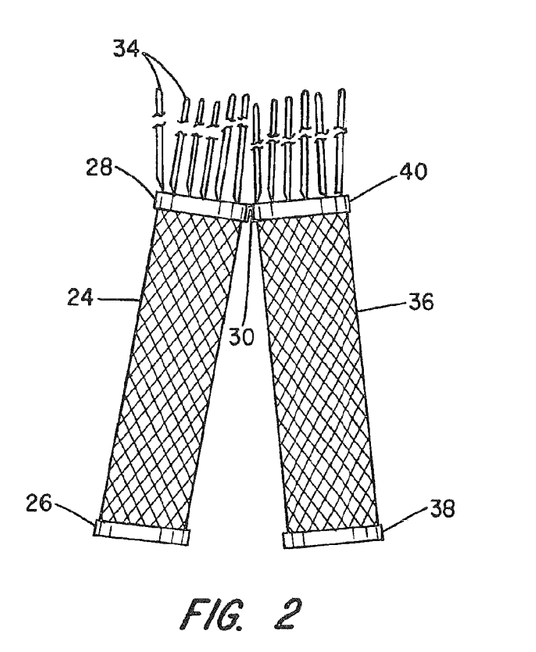
FIG. 2 is side view of two legs of the device of FIG. 1 after braiding and separation of the two-piece mandrel.

In FIG. 2, the central shaft of the mandrel has been removed so that the two halves of the mandrel may be separated and manipulated relative to each other to assume the relative positioning shown in the Figure. For example, the upper mandrel for the second leg may be turned upside down and pivoted about the hinge 30 as shown. The wire loops 34 are shown in the top view in FIG. 3. Note that the hinge area 30 has no loops as none were formed in this region.

As indicated, there are several options involving different procedures for forming the body or trunk portion of the device. Versions of preferred embodiments and examples will be discussed next.

Figure 3:
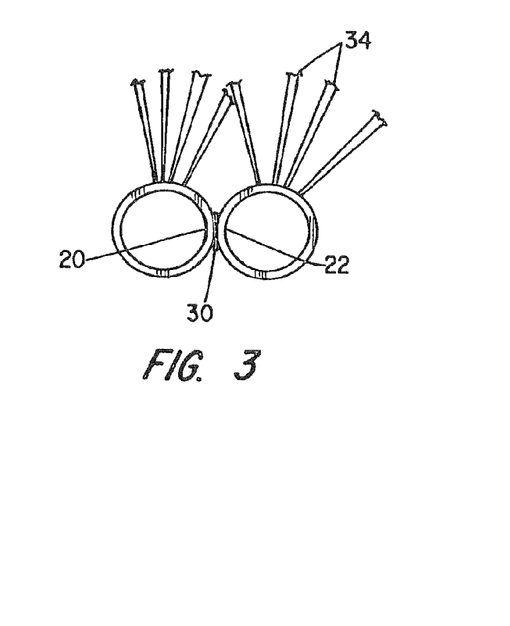
FIG. 3 is a top view of the device shown in FIG. 2 illustrating the filaments available for braiding the trunk portion of the device.

In a first embodiment, the distal ends of the wire loops are not cut or severed and each of the loops 34 is wound with the two wires together onto a spool for braiding the common body or trunk of the stent/graft using double strands. Thus, in the example, 28 spools of two filaments or wires each are available to be placed onto a braider that has at least 28 spool carriers.

In an alternate embodiment, the wire loops are severed toward the ends to form two wires of substantially equal length from each original loop. The two wires are wound on separate spools for placement on a braider including at least (2 times 28) or 56 spool carriers.

Figure 4:
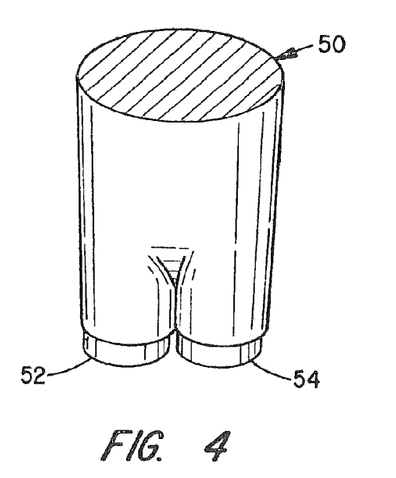
FIG. 4 is a perspective drawing of a trunk mandrel prior to assembly to the leg mandrels.

FIG. 4 illustrates one shape of a mandrel at 50, which may be solid or hollow, for forming the common body or trunk of the stent or graft. There are two pilot diameters or leg extensions 52 and 54 for insertion into the corresponding two-leg mandrels. The now three-part mandrel is secured together by fasteners or other known means and mounted into the braider in a well known manner for braiding the third region or common body or trunk configuration of the device. The corresponding spools are loaded onto the spool carriers as well.

Figure 5:
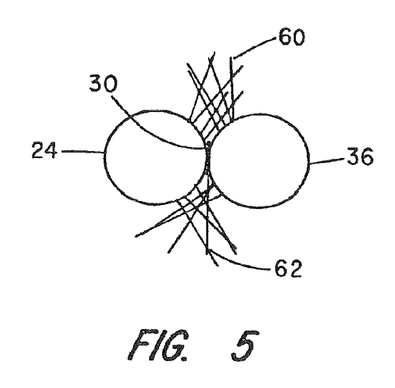
FIG. 5 is a top view of the legs indicating an area for optional manual braiding.

FIG. 5 illustrates an area of transition between the stent/graft leg diameter and the trunk diameter where it may be advisable to optionally hand braid about 4-8 wires of each side of the device as at 60 and 62 to bridge the diameter transition prior to beginning of the machine braiding for the trunk. To do this, the spools involved in the hand braiding are removed from the carrier and then returned to the carrier prior to full machine braiding. This optional process provides smaller openings in the stent/graft between wires in the leg to crotch to trunk transition and makes for a less open device lattice.

As indicated in one embodiment, the 28 pairs of wires are braided together over the mandrel in FIG. 4 for the desired length of the trunk. The braiding is stopped and the filaments or wires are taped or clamped to the mandrel. The wires leading to the spools are cut and the mandrel assembly and braided device are removed from the braider. A finished device in accordance with the embodiment 70 is shown in FIG. 6. The trunk portion with the mesh of double filament loops is shown at 72.

In an alternative embodiment, the severed loops on 56 individual spools of wire are braided together over the trunk mandrel 50 in FIG. 4 for the length of the trunk shown in the embodiment 80 in FIG. 7 as 82. The braiding is then stopped and the wires are taped or clamped to the mandrel. The wires leading to the spools are cut and the mandrel assembly and braided device are removed from the braider. The finished device 80 has a trunk portion braided from single filaments or wires as is shown in FIG. 7.

In the embodiment with the loop braid, the final braiding of the trunk may be accomplished on the same original 32 carrier braider used for braiding the legs, but four of the spools, i.e., every 8th spool, would be empty. However, this would cause the final device to exhibit gaps between some of the braided wires. This is not as desirable as using a braider with the exact number of needed spool carriers. The gaps can be manually spaced more evenly prior to the final device heat treatment to be discussed in the following. Braiders are available in a wide variety of spool carrier numbers such as 4-200 or more in increments of four carriers as offered, for example, by Steeger USA, Spartanburg, S.C.

The heat treatment process follows the braiding of the device. In the case where the braiding process was accomplished on a mandrel that equals the final device size, the braid may remain on the mandrel if the mandrel was made of metal or a material able to adequately handle the temperature of the device heat treatment. Heat treatment techniques are generally known to those skilled in the art.

U.S. Pat. No. 5,725,552 to Kotula et al., incorporated herein in entirety by reference, for example, describes in great detail the heat treatment of braided medical devices made of nitinol wire and the process of confining the device in a mold of the desired final device shape during the heat treatment to set the final device shape in memory. In this regard, it has been found that holding a nitinol fabric or braid at 500-550.degree. C. for a period of about 1-30 minutes, depending on the hardness or softness desired, will tend to set the braid in the shape held during the heat treatment. The materials used to hold the braid in place must be suitable for the temperature range of the heat treatment. For example, the tape if used to hold the braid down may not be suitable, so a metal clamp may be substituted or other means known in the art.

The devices shown in FIGS. 6 & 7 show a slight amount of flare at the trunk as at 74 and 84 and the leg ends as at 76 and 78 (FIG. 6) which can be molded in during a heat set process by holding the braid in the flared condition during the heat set. Any gaps between wires, such as occurring from braiding 28 wires on a 32 spool carrier braiding machine may also be manually repositioned as desired. After heat treatment, they will retain the repositioned shape.

If the braiding mandrel is not the desired final heat set shape for the device, the braided device may be removed from the mandrel and placed in a separate mold to produce the desired shape for heat treatment. After heat treatment and shape setting, the braid will resist unraveling without the need for clamps or other retention means. The flared ends of the trunk and legs have been found to assist the device in seating against the artery walls and, in addition, help prevent the wires from catching on other devices that may be passed through the stent or graft. Preferably, the trunk and legs are sized to be somewhat larger (example 5-30%, preferably 15-20%) in the stent/graft relaxed state than the size of the artery in which they are to be placed, to thereby exert outward pressure on the arterial wall to aid in device seating and retention.

Heat set stents or grafts fabricated by the present braiding process are easily collapsed to a small diameter for delivery through an intravascular catheter lumen by pulling on the trunk and leg ends and stretching the braided wires along the longitudinal axis of the device. Once the device is positioned within the catheter and delivered to the treatment site, the stent/graft may be urged out of a catheter lumen end opening. The released device will self expand to its heat set memorized size or against the arterial wall if the artery is smaller. It will be appreciated that the design of the delivery catheter is somewhat more complex for a branched stent or graft.

Examples of such delivery devices are illustrated in detail in U.S. Pat. No. 6,409,750 to Hyodoh et al. and U.S. Pat. No. 6,953,475 to Shaolian et al.

The branched braided configuration may be used as a stand alone stent or the braid may be a component of a graft whereby a polyester or other braided polymer or woven fabric may be added to the outside of the braided metal structure to serve as a sealing surface to the graft. In this type of configuration, the braided metal expansion characteristics urge the graft fabric out against the arterial wall. The fabric may be attached to the braid by suture as an example or by other means known in the graft art. Alternatively, the polyester or other braided polymer or woven fabric may be added to the inside of the braided metal structure and attached by suture.

Another embodiment of the graft consists of braiding a separate polyester filament using the same techniques as described for the metal filaments or wires. In this embodiment, the braided polymer branched graft material is placed over the heat set metal braid structure and the polymer braid sutured to the metal braid for retention. Alternatively, the branched graft material may be placed within the metal braided structure and sutured to the metal structure. By using similar pitch and pick count for both the metal braid and polymer braid the device can easily collapse and self expand as a unitary device. It should be noted that the underlaying or overlaying polyester or other braided polymer may be fabricated of multiple independent components attached to the metal structure.

In still another embodiment the graft is made using the same braiding process but the single plurality of filaments used to fabricate the graft consists of a combination of metal and polymer filaments braided together in a single operation. The number of metal and polymer filaments and the ratio of metal to polymer may be altered as desired to obtain sufficient self expansion force and adequate polymer density for sealing of the graft. The process allows for a great deal of flexibility in graft design.

The present stent or graft braiding process, unlike other techniques, provides for fabrication of a one piece tubular framework device whereby the legs are connected by a hinge and the legs and trunk are fabricated from a single plurality or array of filaments. It will be appreciated that the legs may be the same or unequal in length, the same or unequal in diameter and of a constant (uniform) or vary in diameter along the length thereof (longitudinal axis) as desired in a particular application.

Although the example device illustrated is for the treatment of an abdominal aortic aneurysm involving the iliac bifurcation, it will be appreciated that the process for braiding and the resulting device is more broadly applicable and not limited to a branched stent or branched graft and a process for fabricating a branched stent or graft for treating a particular condition. There are numerous locations within the body where such a branched stent or graft may be needed and the process is suitable for other configurations as well as the inverted Y stent or graft illustrated. For example, it is anticipated that a side branch can be fabricated off a main braided tubular body in the manner of this invention by creating loops of filaments in a circular pattern at the location of the intended side branch. Such a process involves stopping the braiding machine as braid wires cross the side branch location, creating the loops, and repeating the process until the branch take off area is passed by the braiding. Once the main tube is braided, the loops may be used to braid the side branch.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

That which is claimed:

1. A method of fabricating a braided device suitable for implantation in an anatomical structure, the braided device having a first leg, a second leg, and a common body attached to the first leg and the second leg, the method comprising:
    (a) braiding, in a first orientation, a first end of a plurality of filaments to form the first leg;
    (b) braiding, in the first orientation, a second end of the plurality of filaments to form the second leg, wherein, in the first orientation, the first leg and the second leg are substantially axially aligned;
    (c) moving the first leg and the second leg to a second orientation, in which the first leg and the second leg are substantially non-aligned; and
    (d) braiding, in the second orientation, an intermediate portion of at least some of the plurality of filaments to form the common body attached to the first leg and the second leg, wherein the intermediate portion extends between the first end and second end.

2. The method of claim 1 wherein braiding of the intermediate portion comprises braiding a subset of the plurality of filaments to form the common body.

3. The method of claim 2, further comprising designating a number of the plurality of filaments as the subset prior to braiding the second end of the plurality of filaments to form the second leg.

4. The method of claim 3, further comprising forming extended loops from the intermediate portion of the number of the plurality of filaments designated as the subset.

5. The method of claim 4, further comprising securing the loops to prevent them from being entangled during the braiding of the second end of the plurality of filaments to form the second leg.

6. The method of claim 4, further comprising severing each of the loops prior to the braiding of the common body.

7. The method of claim 1, wherein moving the first leg and the second leg to a second orientation comprises rotating one of the first leg or the second leg about a number of filaments designated as a hinge zone.

8. The method of claim 7, wherein the number of filaments designated as the hinge zone connect the first leg directly to the second leg.

9. The method of claim 1, wherein braiding of the first end of the plurality of filaments to form the first leg and braiding of the second end of the plurality of filaments to form the second leg is done on a first tubular mandrel comprising a two-piece mandrel assembled from two temporarily joined mandrel parts.

10. The method of claim 9, wherein braiding of the intermediate portion to form the common body is done on a second tubular mandrel, wherein the method further comprises attaching both mandrel parts to the second tubular mandrel prior to braiding the common body.

11. An intraluminal device, comprising:
    a first leg having a braided structure formed by a first end of a plurality of filaments;
    a second leg having a braided structure formed by a second end of the plurality of filaments; and
    a common body coupled to the first leg and the second leg having a braided structure formed by an intermediate portion of at least some of the plurality of filaments, wherein the intermediate portion extends between the first end and the second end.

12. The intraluminal device of claim 11, wherein the plurality of filaments comprises a shape memory alloy.

13. The intraluminal device of claim 12, further comprising a second braided device comprising non-metallic filaments, wherein the second braided device is disposed adjacent to the braided device comprising the shape memory alloy to form a composite graft device.

14. The intraluminal device of claim 13, wherein the second braided device is secured to the braided device comprising the shape memory alloy.

15. The intraluminal device of claim 13, wherein the second braided device and the braided device comprising the shape memory alloy are braided using a similar pitch and pick count.

16. The intraluminal device of claim 11, wherein one or more ends of the braided device are flared.

17. The intraluminal device of claim 11 further comprising a hinge zone connecting the first leg directly to the second leg.

18. The intraluminal device of claim 17, wherein the hinge zone represents about ⅛ to about ¼ of the plurality of filaments.

19. The intraluminal device of claim 11, wherein the plurality of filaments comprises a combination of metallic and non-metallic filaments.

20. The intraluminal device of claim 11, wherein the common body is formed by an intermediate portion of a subset of the plurality of filaments.

* * * * *